United States Patent [19]
Geerlings et al.

[11] Patent Number: 5,958,985
[45] Date of Patent: Sep. 28, 1999

[54] PROCESS FOR THE PREPARATION OF HYDROCARBONS

[75] Inventors: Jacobus Johannes Cornelis Geerlings; Arend Hoek; Hans Michiel Huisman; Peter William Lednor, all of Amsterdam, Netherlands

[73] Assignee: Shell Oil Company, Houston, Tex.

[21] Appl. No.: 08/989,430

[22] Filed: Dec. 12, 1997

[30] Foreign Application Priority Data

Dec. 13, 1996 [EP] European Pat. Off. ............. 96203538

[51] Int. Cl.$^6$ ............................ C07C 27/00; B01J 23/32; B01J 23/00
[52] U.S. Cl. ....................... 518/700; 518/715; 502/324; 502/325
[58] Field of Search .................. 518/700, 715; 502/324, 325

[56] References Cited

U.S. PATENT DOCUMENTS

| | | | |
|---|---|---|---|
| 4,463,101 | 7/1984 | Dwyer et al. | 502/74 |
| 4,874,732 | 10/1989 | Miller. | |
| 5,162,284 | 11/1992 | Soled et al. | 502/324 |

FOREIGN PATENT DOCUMENTS

| | | |
|---|---|---|
| 0 071 770 A2 | 8/1982 | European Pat. Off. . |
| 97/00231 | 3/1997 | WIPO . |

*Primary Examiner*—Paul J. Killos
*Assistant Examiner*—J. Parsa

[57] ABSTRACT

A process for the preparation of hydrocarbons by catalytic reaction of carbon monoxide with hydrogen in which reaction a feed comprising hydrogen and carbon monoxide is contacted at elevated temperature and pressure with a catalyst comprising cobalt and manganese in which catalyst the cobalt/manganese molar ratio is between 14:1 and 7:1 and the GHSV is at least 1600 Nl/l/h. Preferably the cobalt/manganese molar ratio is between 13:1 and 9:1 and the GHSV is between 2700 and 25,000 Nl/l/h. The reaction is especially carried out in a slurry phase regime.

16 Claims, No Drawings

PROCESS FOR THE PREPARATION OF HYDROCARBONS

FIELD OF THE INVENTION

The present invention relates to a process for the preparation of hydrocarbons from synthesis gas, a mixture of carbon monoxide and hydrogen.

BACKGROUND OF THE INVENTION

The catalytic preparation of hydrocarbons from synthesis gas is well known in the art and is commonly referred to as Fischer-Tropsch synthesis.

Catalysts suitable for use in a Fischer-Tropsch synthesis process typically contain a catalytically active metal of Group VIII of the Periodic Table of the Elements (Handbook of Chemistry and Physics, 68th edition, CRC Press, 1987–1988). In particular, iron, nickel, cobalt and ruthenium are well known catalytically active metals for such catalyst. Cobalt has been found to be most suitable for catalysing a process in which synthesis gas is converted into primarily paraffinic hydrocarbons containing 5 or more carbon atoms. In other words, the $C_{5+}$ selectivity of the catalyst is high.

Much research effort has been directed to finding catalysts, especially cobalt based catalysts, and/or process conditions resulting in a higher $C_{5+}$ selectivity than known catalysts at the same or higher activity.

Thus, European patent specification No. 398 420 describes that the $C_{5+}$ selectivity of catalysts comprising cobalt and zirconium, titanium or chromium on a porous carrier, having a small external surface area, can be improved by contacting the catalyst with a synthesis gas having a low hydrogen to carbon monoxide ratio, typically, from 1.1 to 1.2.

European patent specification No. 178 008 discloses cobalt catalysts supported on a porous carrier, wherein most cobalt is concentrated in the rim of the catalyst particle.

European patent specification No. 167 215 discloses a cobalt/zirconia on silica catalyst for use in a fixed catalyst bed which catalyst satisfies a relation between the internal surface area and the external surface area.

European patent specification No. 168 894 discloses an optimal activation procedure to increase the $C_{5+}$ selectivity of a cobalt-based Fischer-Tropsch catalyst.

European patent specification No. 363 537 describes an increase in activity of cobalt catalysts supported on titania, by adding up to 15% by weight of silica to the titania carrier.

European patent application publication No. 498 976 describes catalysts containing cobalt and rhenium supported on a titania carrier. It is claimed that these catalysts have a high volumetric productivity (activity).

European patent application publication No. 71 770 describes a process for the preparation of linear α-olefins from synthesis gas. Inter alia cobalt/manganese and cobalt/vanadium catalysts are claimed to be applicable in this process. The $C_{5+}$ selectivity of a catalyst comprising cobalt and manganese in a ratio of 1:6, is only 50%.

Van der Riet et al. (1986) J. Chem. Soc., Chem. Commun., pages 798–799 describe selective formation of C3 hydrocarbons from carbon monoxide and hydrogen using cobalt-manganese oxide catalysts. The cobalt/manganese ratio is typically 1:1.

International PCT application WO 93/05000 describes a Fischer-Tropsch catalyst comprising cobalt and scandium. Optionally, the catalyst contains additional promoters like thoria and/or other materials such as magnesia and manganese.

"The Fischer-Tropsch and Related Synthesis" by H. H. Storch, N. Golumbic, and R. B. Anderson (John Wiley and Sons, New York, 1951), referred to in International PCT Application WO 93/05000 provides a review of early work on Fischer-Tropsch catalysts, including catalysts comprising cobalt and manganese and/or vanadium. On page 120 reference is made to experiments in which it was found that cobalt-vanadium oxide and cobalt-manganese oxide catalysts were inactive as Fischer-Tropsch catalysts. However, on page 198 reference is made to experiments in which it was found that a catalyst containing cobalt and manganese in a atomic ratio of 6.2:1 had a higher $C_{5+}$ selectivity as compared to a catalyst containing cobalt and thoria, but at a significantly lower synthesis gas conversion.

Australian patent application No. 46119/85 describes a catalyst containing cobalt, silica and a base or alkaline material, typically an alkali or alkaline earth metal. Optionally additional promoters may be present chosen from salts of elements chosen from the group of aluminum, magnesium, zinc, copper, manganese, chromium, vanadium, germanium, boron, molybdenum, lanthanum, the Rare Earths and the like or combinations thereof and arsenic or antimony. It is claimed that these catalysts have a high selectivity towards lower boiling 1-alkenes.

Despite the research effort in this field there is still room for improvement. Accordingly, it would be desirable if catalysts or process conditions could be found which result in a still higher $C_{5+}$ selectivity at the same or, preferably, higher activity than known catalysts or process conditions.

SUMMARY OF THE INVENTION

It has now surprisingly been found that for cobalt/manganese catalysts having different cobalt/manganese molar ratios the best $C_{5+}$ selectivity and/or the highest activity depends on the Co/Mn molar ratio for each GHSV value of the synthesis gas. For relatively low cobalt/manganese ratios it appears that relatively high synthesis gas GHSV values not only result in the highest $C_{5+}$ selectivities, but also in the most active catalysts, i.e. the highest conversion of synthesis gas, when compared with cobalt/manganese catalysts having higher cobalt/manganese molar ratios which are used at relatively low GHSV values. The $C_{5+}$ selectivity is calculated as the percentage $C_{5+}$ compounds of the total amount of carbon and hydrogen containing compounds formed.

Thus, the present application relates to a process for the preparation of hydrocarbons by catalytic reaction of carbon monoxide with hydrogen in which reaction a feed comprising hydrogen and carbon monoxide is contacted at elevated temperature and pressure with a catalyst comprising cobalt and manganese, wherein the cobalt/manganese molar ratio is between 14:1 and 7:1 and the GHSV is at least 1600 Nl/l/h.

DESCRIPTION OF THE PREFERRED EMBODIMENTS

In a preferred embodiment the process of the present invention uses a catalyst in which the cobalt/manganese molar ratio is between 13:1 and 9:1, more especially between 12.5:1 and 10:1.

The GHSV of the synthesis gas in the process of the present invention is suitably at least 2100 Nl/l/h, preferably at least 2700 Nl/l/h, more preferably at least 3200 Nl/l/h. The GHSV will usually be less than 25,000 Nl/l/h, preferably less than 16,000 Nl/l/h, more preferably less than 10000 Nl/l/h. The term GHSV is well known in the art, and relates to the gas per hour space velocity, i.e. the volume of synthesis gas in Nl (i.e. at the standard temperature of 25° C. and the standard pressure of 1 bar (100,000 Pa)) which is contacted in one hour with one liter of catalyst particles, i.e. excluding interparticular void spaces. In the case of especially a fixed bed catalyst, the GHSV may also be expressed as per liter of catalyst bed, i.e. including interparticular void space. In that case a GHSV of 1600 Nl/l/h on catalyst particles corresponds to about 1000 Nl/l/h on catalyst bed.

Usually the synthesis gas mainly comprises carbon monoxide and hydrogen, together with small amounts methane, carbon dioxide, nitrogen and other inerts. Suitably at least 70 percent of the synthesis gas is hydrogen and carbon monoxide, preferably at least 80 percent, more preferably at least 90 percent. The space velocity is calculated on the amount of hydrogen and carbon monoxide, i.e. the inerts are not included. The volume of catalyst is calculated on dry catalyst, excluding the void spaces between the catalyst particles.

The catalyst to be used in the process of the present invention suitably comprises a carrier, especially a porous carrier. In a preferred embodiment, the carrier is a refractory oxide carrier. Examples of suitable refractory oxide carriers include alumina, silica, titania, zirconia or mixtures thereof, such as silica-alumina or physical mixtures such as silica and titania. Preferably, the carrier comprises titania, zirconia or mixtures thereof.

According to a further preferred embodiment, the carrier comprising titania, zirconia or mixtures thereof, may further comprise up to 50% by weight of another refractory oxide, typically silica or alumina. More preferably, the additional refractory oxide, if present, comprises up to 20% by weight, even more preferably up to 10% by weight, of the carrier.

The carrier most preferably comprises titania, in particular titania which has been prepared in the absence of sulphur-containing compounds. An example of such preparation method involves flame hydrolysis of titanium tetrachloride. It will be appreciated that the titania powder derived from such preparation method may not be of the desired size and shape. Thus, usually a shaping step is required to prepare the carrier. Shaping techniques are well known to those skilled in the art and include pelletising, extrusion, spray-drying, and hot oil dropping methods.

The amount of cobalt present in the catalyst may vary widely. Typically, the catalyst comprises 1–100 parts by weight of cobalt per 100 parts by weight of carrier, preferably, 3–60 parts by weight, more preferably, 5–40 parts by weight. The above amounts of cobalt refer to the total amount of cobalt, on the basis of cobalt metal, and can be determined by known elemental analysis techniques.

In addition to manganese, the catalyst may comprise one or more additional promoters known to those skilled in the art. Preferably any additional promoters are selected from Group IIIB, IVB, the noble metals of Group VIII of the Periodic Table or rhenium, niobium or tantalum, more preferably from Group IVB, the noble metals of Group VIII of the Periodic Table or rhenium, niobium or tantalum. Especially preferred additional promoters include zirconium, titanium, ruthenium, platinum, vanadium, palladium and/or rhenium. The amount of additional promoter, if present, is typically between 0.1 and 150 parts by weight, for example between 1 and 50 parts by weight, per 100 parts by weight of carrier.

Typically, the catalysts to be used in the process according to the present invention do not contain alkali or alkaline earth metals, apart from possible impurities introduced with starting materials in the preparation process of the catalysts of the present invention. Typically, the atomic ratio of alkali or alkaline earth metals to cobalt metal is less than 0.01, preferably, less than 0.005.

The catalyst to be used in the process according to the present invention may suitably be prepared by methods known to those skilled in the art, such as by precipitating the catalytically active compounds or precursors onto a carrier; spray-coating, kneading and/or impregnating the catalytically active compounds or precursors onto a carrier; and/or extruding one or more catalytically active compounds or precursors together with carrier material to prepare catalyst extrudates.

It will be appreciated by those skilled in the art that the most preferred method of preparation may vary, depending e.g. on the desired size of the catalyst particles. It belongs to the skill of the skilled person to select the most suitable method for a given set of circumstances and requirements.

A preferred method of preparing the catalyst for the present invention is by impregnating the catalytically active compounds or precursors onto a carrier. Thus, typically, the carrier is impregnated with a solution of a cobalt salt and a solution of a manganese salt. Preferably, the carrier is impregnated simultaneously with the respective metal salts. Thus, according to a preferred embodiment, the process for preparing the catalyst for the present invention comprises co-impregnating the carrier with a solution of a cobalt salt and a manganese salt. In case a cobalt and manganese containing catalyst is to be prepared, most preferably a highly concentrated solution is employed. A suitable method to arrive at such a concentrated solution is to use a mixture of molten cobalt nitrate and manganese nitrate salts (i.e. a solution obtained by dissolving the salts in their own crystal water). In a preferred embodiment the volume of the impregnation solution is substantially the same (i.e. suitably between 85% and 105%, preferably between 90% and 100%, more preferably about 95%) as the pore volume of the carrier (pore volume impregnation).

The surface area of the catalyst carrier is suitably more than 0.5 $m^2/g$, especially more than 10 $m^2/g$, preferably more than 25 $m^2/g$, more preferably more than 35 $m^2/g$. The surface area is suitably below 400 $m^2/g$, preferably below 200 $m^2/g$. The surface area is especially between 40 and 100 $m^2/g$.

The pore volume of the catalyst carrier is preferably at least 0.10 ml/g, more preferably between 0.25 and 1.5 ml/g, still more preferably between 0.30 and 1.0 ml/g. The pore volume is suitably determined by Hg porosimetry according to ASTM D 4284-92 up to a pressure of 60000 psi (4.1 kbar).

The impregnation treatment is typically followed by drying and, optionally, calcining. Drying is typically carried out at a temperature of 50 to 300° C. for up to 24 hours, preferably, 1 to 4 hours.

Calcination is typically carried out at a temperature between 200 and 900° C., preferably, between 250 and 600° C. The duration of the calcination treatment is typically from 0.5 to 24 hours, preferably from 1 to 4 hours. Suitably, the calcination treatment is carried out in an oxygen-containing atmosphere, preferably air. It will be appreciated that the average temperature during the calcination treatment will normally be higher than the average temperature during the drying treatment.

The process according to the present invention relates a process for the preparation of hydrocarbons from synthesis gas. Typically in that process, at least part of the cobalt is present in its metallic state.

Therefore, it is normally advantageous to activate the catalyst prior to use by a reduction treatment, in the presence of hydrogen at elevated temperature. Typically, the reduction treatment involves treating the catalyst at a temperature in the range from 100 to 450° C. for 1 to 48 hours at elevated pressure, typically from 1 to 200 bar abs. Pure hydrogen may be used in the reduction treatment, but it is usually preferred to apply a mixture of hydrogen and an inert gas, like nitrogen. The relative amount of hydrogen present in the mixture may range between 0 and 100% by volume.

According to one preferred embodiment, the catalyst is brought to the desired temperature and pressure level in a nitrogen gas atmosphere. Subsequently, the catalyst is contacted with a gas mixture containing only a small amount of hydrogen gas, the rest being nitrogen gas. During the reduction treatment, the relative amount of hydrogen gas in the gas mixture is gradually increased up to 50% or even 100% by volume.

If possible, it is preferred to activate the catalyst in-situ, that is inside the reactor. European patent application No. 95203040.1 describes an in-situ catalyst activation process which comprises contacting the catalyst in the presence of hydrocarbon liquid with a hydrogen-containing gas at a hydrogen partial pressure of at least 15 bar abs., preferably at least 20 bar abs., more preferably at least 30 bar abs. Typically, in this process the hydrogen partial pressure is at most 200 bar abs.

The process of the present invention to prepare hydrocarbons is typically carried out at a temperature in the range from 125 to 350° C., preferably 175 to 275° C. The pressure is typically in the range from 5 to 150 bar abs., preferably from 5 to 80 bar abs., in particular from 5 to 50 bar abs.

Hydrogen and carbon monoxide (synthesis gas) is typically fed to the process at an atomic ratio in the range from 0.5 to 4, especially from 1 to 3. It is known that low hydrogen to carbon monoxide molar ratios will increase the $C_{5+}$ selectivity of Fischer-Tropsch catalysts. It has now been found that the $C_{5+}$ selectivity of the catalyst according to the present invention is remarkably high, even when using synthesis gas having a high hydrogen to carbon monoxide atomic ratio. In a preferred embodiment of the hydrocarbon synthesis process of the present invention, the hydrogen to carbon monoxide atomic ratio is in the range from 1.5 to 2.5. It is observed that when non-converted hydrogen and/or carbon monoxide is recirculated over the catalyst bed, it is possible to choose the circumstances in such a way that the catalyst is contacted with a synthesis gas having a substantial lower $H_2/CO$ ratio that the feed synthesis gas. Thus the selectivity to longer hydrocarbon chains may be further improved.

The selectivity of the process of the present invention to $C_{5+}$ hydrocarbons (i.e. hydrocarbons containing five carbon atoms or more is suitably more than 80%, preferably more than 85%, more preferably more than 88% of the total amount of hydrocarbons formed. Usually the $C_{5+}$ selectivity will be between 86 and 92% or even 94%, but higher values may be obtained.

The process for the preparation of hydrocarbons may be conducted using a variety of reactor types and reaction regimes, for example a fixed bed regime, a slurry phase regime or an ebullating bed regime. It will be appreciated that the size of the catalyst particles may vary depending on the reaction regime they are intended for. It belongs to the skill of the skilled person to select the most appropriate catalyst particle size for a given reaction regime.

Further, it will be understood that the skilled person is capable to select the most appropriate conditions for a specific reactor configuration and reaction regime. For example, the preferred gas per hour space velocity may depend upon the type of reaction regime that is being applied. Thus, if it is desired to operate the hydrocarbon synthesis process with a fixed bed regime, preferably the gas per hour space velocity is chosen in the range from 1600 to 5120 Nl/l/h. If it is desired to operate the hydrocarbon synthesis process with a slurry phase regime, preferably the gas per hour space velocity is chosen in the range from 2400 to 12000 Nl/l/h.

The hydrocarbon synthesis may be carried out in a fixed bed, a fluid bed or (slurry type) bubble column reactors. All reactor type are well known in the prior art and fully described in available literature. In a preferred embodiment of the invention the reaction is carried out in a slurry phase regime. Catalyst particle size in a slurry phase regime may vary between 5 micron and 1 mm, preferable between 10 and 200 microns, more preferably between 20 and 100 micron (mean particle size). Fully back mixed conditions may be used as well as plug flow conditions, as well as condition between these two extremes.

The hydrocarbons obtained in the process of the present invention are especially paraffinic hydrocarbons, more especially saturated unbranched alkanes. Smaller amounts (i.e. up to 5 percent) of alkenes or oxygen containing alkanes may be obtained. The high-boiling part of the paraffinic product may be converted into middle distillates by the use of a catalytic hydrotreatment. Middle distillates are boiling in the kerosene and gasoil region, usually between 80° C. and 300° C., especially between 100 and 240° C. The feed for the hydrotreatment is chosen at least the part of the product whose initial boiling point lies above the final boiling point of the heaviest middle distillates desired as end product, although also the complete product may be used as feed for the catalytic hydrotreatment in order to improve simultaneously the properties of the directly obtained middle distillates (reduction of unsaturated compounds and oxygenates, hydroisomerisation). The catalytic hydrotreatment is carried out by contacting the fraction to be treated at elevated temperature and pressure and in the presence of hydrogen with a catalyst containing one or more metals with hydrogenation activity. Examples of suitable catalysts are catalysts containing nickel and or cobalt and in addition molybdenum and/or tungsten supported on a carrier such as alumina or silica-alumina. In the catalytic treatment it is preferred to use a catalyst containing one or more noble metals from Group VIII of the Periodic Table supported on a carrier. Preference is given to catalysts comprising platinum or palladium.

The invention will now be illustrated further by means of the following non limiting Examples.

EXAMPLE 1

Commercially available titania particles (54.97 g, Degussa, P-25) were spraydried, (dried at 120° C. for 2 hours), calcined at 500° C. for 2 hours, PV 0.59 ml/g) were impregnated (pore-volume impregnation) at 75° C. with a melt of cobalt and manganese nitrate (57.53 g, made from 55.63 g cobalt nitrate hydrate and 3.82 g manganese nitrate hydrate). The impregnated titania carrier was equilibrated (slowly stirred) for 1 hour at 55° C. After that the impregnated carrier was dried (2 hours, 150° C.) and calcined (2 hours, 500° C., increase 120° C./h) under an air flow of 150 Nl/1/h in a rotating kiln. Co/Mn molar ratio 12.34.

EXAMPLE 2

Example 1 was repeated, using 25 g titania and 25.38 g melt (23.62 g cobalt nitrate, 2.20 g manganese nitrate). Co/Mn molar ratio 9.26.

EXAMPLE 3

Comparative

Example 1 was repeated, using 24.90 g titania and 23.45 g melt (22.73 g cobalt nitrate, 1.25 g manganese nitrate). Co/Mn molar ratio 16.12.

EXAMPLE 4

Comparative

Example 1 was repeated, using 25.01 g titania and 25.37 g melt (22.57 g cobalt nitrate, 3.13 g manganese nitrate). Co/An molar ratio 6.25.

EXAMPLE 5

Hydrocarbon Synthesis

The catalysts prepared in examples 1, 2, 3 and 4 were tested in a process for the preparation of hydrocarbons. Microflow reactors A, B, C and D, containing 10 g of catalysts 1, 2, 3 and 4 respectively, were heated to a temperature of 260° C., and pressurised with a continuous flow of nitrogen and hydrogen gas. During reduction, the relative amount of hydrogen in the mixture was gradually increased from 0%v to 100%v. The water concentration in the off-gas was kept below 3000 ppmv.

After the reduction, the pressure was increased to 26 bar abs. using a mixture of hydrogen and carbon monoxide at a H2/CO molar ratio of 1.7:1. The GHSV was 3840 N1/1/h calculated on catalyst volume excluding interparticular voids.

The reaction temperature was chosen in such a way that the space time yield (STY), expressed as grams hydrocarbon product per liter catalyst bed per hour, was the same in all experiments (100 g/1/h). The $C_{5+}$ selectivity, expressed as a weight percentage of the $C_{5+}$ hydrocarbons of the total amount of hydrocarbons produced, was determined for each of the reactors after 100 hours of operation. The results are set out in Table I.

TABLE I

| Reactor: | A | B | C | D |
| --- | --- | --- | --- | --- |
| Catalyst: | 1 | 2 | 3 | 4 |
| Co/Mn ratio: | 12.3 | 9.3 | 16.1 | 6.3 |
| $C_{5+}$ selectivity: | 89.0 | 88.4 | 84.4 | 87.3 |
| T (° C.): | 214 | 217 | 220 | 229 |

In a second comparison example catalysts were tested at a GHSV of 1040 N1/1/h. It appeared that out of three catalysts, one containing cobalt and no manganese, the other two having a Co/Mn molar ratio of 20 respectively 10, the catalyst with the Co/Mn molar ratio of 20 was the most active and showing the highest $C_{5+}$ selectivity. The catalyst used in this comparison example were made in the same way as catalysts 1 to 4 described above. The catalysts were tested at the same way as described above, at 200° C. The results are summarised in Table II.

TABLE II

| Reactor: | E | F | G |
| --- | --- | --- | --- |
| Catalyst: | I | II | III |
| Co/Mn ratio: | — | 20 | 10 |
| $C_{5+}$ selectivity: | 89 | 91 | 87 |
| STY (g/l/h): | 70 | 100 | 87 |

We claim:

1. A process for the preparation of hydrocarbons by catalytic reaction of carbon monoxide with hydrogen in which reaction $C_{5+}$ selectivity and/or activity is optimized by matching a cobalt/manganese molar ratio of a catalyst with a GHSV of a gas feed, said process comprising contacting a feed comprising hydrogen and carbon monoxide at elevated temperature and pressure with a catalyst comprising cobalt and manganese in which catalyst the cobalt/manganese molar ratio is between 14:1 and 7:1 and the GHSV of the feed is at least 1600 N1/1/h.

2. A process according to claim 1 wherein the cobalt/manganese ratio is between 13:1 and 9:1.

3. A process according to claim 1 wherein the GHSV is between 2100 and 25,000 N1/1/h.

4. A process according to claim 3 wherein the GHSV is between 2700 and 16,000 N1/1/h.

5. A process according to claim 1 wherein the catalyst comprises a porous carrier.

6. A process according to claim 5 wherein the refractory oxide is alumina, zirconia, silica or titania.

7. A process according to claim 5 wherein the catalyst is prepared by impregnation of the carrier with the catalytically active compounds or the precursors for the catalytically active compounds.

8. A process according to claim 5 wherein the catalyst comprises 3–60 parts by weight of cobalt per 100 parts by weight of carrier.

9. A process according to claim 1 wherein at least part of the cobalt is in the metallic state.

10. A process according to claim 1 wherein the temperature is in the range from 175 to 275° C. and the pressure is between 5 and 50 bar abs.

11. A process according to claim 1 wherein the hydrocarbon synthesis is carried out in a slurry phase regime.

12. A process according to claim 1 wherein the $C_{5+}$ selectivity is at least 85%.

13. A process according to claim 12 wherein the $C_{5+}$ selectivity is at least 88%.

14. A process according to claim 5 wherein the catalyst comprises a refractory oxide carrier.

15. A process according to claim 6 wherein the refractory oxide is titania.

16. A process according to claim 7 wherein the catalyst is prepared by impregnation of the carrier with the catalytically active compounds by pore volume impregnation.

* * * * *